United States Patent [19]

Jones

[11] 4,349,548
[45] Sep. 14, 1982

[54] OCTAHYDROBENZO[6,7]CYCLOHEPT[1,2-b]-1,4-OXAZINES, COMPOSITIONS AND USE

[75] Inventor: James H. Jones, Blue Bell, Pa.

[73] Assignee: Merck & Co., Inc., Rahway, N.J.

[21] Appl. No.: 323,771

[22] Filed: Nov. 20, 1981

[51] Int. Cl.$^3$ .................. C07D 265/34; A61K 31/535
[52] U.S. Cl. ........................... 424/248.4; 424/248.58; 544/101
[58] Field of Search .................... 544/101; 424/248.4, 424/248.58

[56] References Cited

FOREIGN PATENT DOCUMENTS 34546  8/1981  European Pat. Off. .

OTHER PUBLICATIONS

Yupraphat et al., Liebigs Ann. Chem., 738, 79–85, (1970).
Khanna et al., J. Indian Chem. Soc., 51, 289–303, (1974).

Primary Examiner—Robert W. Ramsuer
Attorney, Agent, or Firm—William H. Nicholson; Mario A. Monaco

[57] ABSTRACT

4-Substituted-2,3,4,4a,5,6,7,11b-octahydrobenzo[6,7]cyclohept[1,2-b]-1,4-oxazines are prepared from the corresponding 6-(substituted amino)-6,7,8,9-tetrahydro-5H-benzocycloheptene-5-ol. The trans-4-substituted-2,3,4,4a,5,6,7,11b-octahydrobenzo[6,7]cyclohept[1,2-b]-1,4-oxazines have α-adrenergic agonist and tetrabenazine antagonist activity.

9 Claims, No Drawings

OCTAHYDROBENZO[6,7]CYCLOHEPT[1,2-b]-1,4-OXAZINES, COMPOSITIONS AND USE

BACKGROUND OF THE INVENTION

This invention is concerned with novel compounds of structural formula:

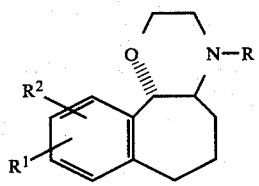

or a pharmaceutically acceptable salt thereof wherein R is $C_{1-4}$ alkyl, $C_{2-5}$ alkenyl or phenyl-lower alkyl; and $R^1$ and $R^2$ are independently hydrogen, $C_{1-4}$ alkoxy or hydroxy.

It is also concerned with processes for the synthesis of the novel compounds, pharmaceutical formulations thereof and with the use of the novel compounds for the treatment of depression and hypertension.

The cis- and trans-isomers of the starting materials, 6-(substituted amino)-6,7,8,9,-tetrahydro-5H-benzocycloheptene-5-ol are described by Yupraphat et al. in Liebigs Ann. Chem., 738, 79–85 (1970) and also Khanna et al., J. Ind. Chem Soc., 51 289 (1974), and are said to have weak sympathomimetic properties.

Surprisingly, it has been found that ring closing through the amino and hydroxyl groups to form a cis- or trans-fused oxazine ring serves to fix the position of the amino group relative to the benzo structure, and the trans- compounds lose their dopaminergic activity and pick up α-adrenergic agonist (antihypertensive) activity and tetrabenazine antagoinst (antidepressant) activities.

DETAILED DESCRIPTION OF THE INVENTION

The novel compounds of this invention are of structural formula:

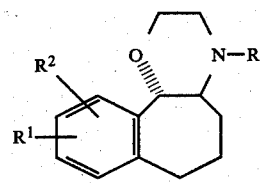

I or a pharmaceutically acceptable salt thereof, wherein R is $C_{1-4}$ alkyl, especially ethyl or propyl, $C_{2-5}$ alkenyl, especially allyl, or phenyl-$C_{1-4}$ alkyl, especially benzyl, and $R^1$ and $R^2$ are independently hydrogen, hydroxy, $C_{1-4}$ alkoxy, especially methoxy, or phenyl-$C_{1-4}$ alkoxy, especially benzyloxy.

The trans isomers of this invention are enantiomeric mixtures which may be separated into individual enantiomers by methods known in the art such as by the formation of diastereomeric salts. Alternatively, each enantiomer can be synthesized from an optically pure starting material.

The pharmaceutically acceptable salts of the novel compounds of this invention are acid addition salts formed from a novel compound and an organic or inorganic acid recognized by the art as providing a pharmaceutically acceptable acid addition salt, such as hydrochloride, hydrobromide, dihydrogen phosphate, sulfate, citrate, pamoate, pyruvate, napsylate, isethionate, maleate, fumarate, or the like.

These salts are readily prepared by mixing solutions of equimolecular amounts of the free base compound and the desired acid in suitable solvents such as water, alcohols, ether or chloroform, followed by recovery of the product by collecting the pecipitated salt or evaporation of the solvent.

The process for preparing the novel compounds is another embodiment of this invention and is represented as follows:

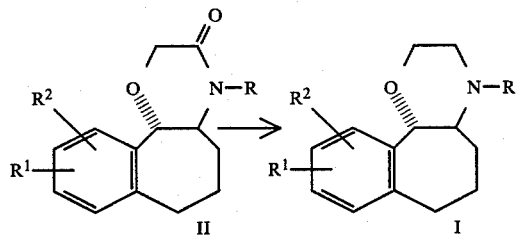

II     I

The novel process comprises the reduction of the oxazinone, II, with a complex metal hydride such as lithium aluminum hydride, or borane in an inert organic solvent such as an ether, for example, tetrahydrofuran, 1,2-dimethoxyethane, tetrahydropyran, or the like at a temperature between about 0° C. and 100° C. Operating procedures normally involve slow addition of the ketone to the reducing agent at room temperature or below, followed by heating to an elevated temperature within the stated range, preferably, the reflux temperature of the solvent, for about ½ to about 4 hours usually about 1–2 hours.

If $R^1$ and/or $R^2$ in the final product is to be hydroxyl, these compounds are prepared from the corresponding $C_{1-14}$ alkoxy compound by treatment with $BBr_3$ or $AlCl_3$ in an alkane such as hexane, or a chlorinated alkane such a methylene chloride or tetrachloroethane between room temperature and reflux temperature for 6 to about 24 hours. Alternatively, they are prepared by hydrogenolysis of the benzyl ethers.

A third embodiment of this invention are the pharmaceutical formulations comprising one of the novel compounds as active ingredient. They may be in any art recognized form suitable for oral use, such as tablets, troches, lozenges, aqueous or oil suspensions, dispersible powders, or granules, emulsions, hard or soft capsules, syrups, or elixirs. For intravenous and intramuscular and subcutaneous use the pharmaceutical compositions may be in any art recognized form of a sterile injectable preparation such as a sterile aqueous or oleaginous solution or suspension. The amount of active ingredient incorporated in a unit dosage of the above described pharmaceutical compositions may be from 1 to 400 mg, and preferably from 5 to 250 mg.

Another embodiment of this invention is the treatment of depression or hypertension by administration of one of the novel compounds. The route of administration can be oral, rectal, intravenous, intramuscular, or subcutaneous. Doses of 1.0 to 200 mg/kg/day and preferably of 5.0 to 100 mg/kg/day of active ingredient are generally adequate, and if preferred it can be administered in divided doses given two to four times daily.

It is to be noted that the precise unit dosage form and dosage level depend upon the requirements of the individual being treated and, consequently, are left to the discretion of the therapist.

EXAMPLE 1

Trans-4-Ethyl-2,3,4,4a,5,6,7,11b-octahydrobenzo[6,7]cyclohept[1,2-b]-1,4-oxazine and hydrogen maleate salt Step A: Preparation of trans-6-(N-ethyl-N-chloroacetylamino)-6,7,8,9-tetrahydro-5H-benzocyclohepten-5-ol A solution of 0.75 ml (0.022 m) of chloroacetyl chloride in 10 ml of methylene chloride was added dropwise to a solution of 2.3 g (0.0112 m) of trans-6-(N-ethylamino)-6,7,8,9-tetrahydro-5H-benzo cyclohepten-5-ol and 3.2 ml (0.023 m) of triethylamine in 90 ml of methylene chloride. The mixture was stirred ½ hour, water is added, and the layers are separated. The organic layer was dried over anhydrous sodium sulfate and concentrated to dryness in vacuo.

Step B: Preparation of trans-4-ethyl-4,4a,5,6,7,11b-hexahydrobenzo[6,7]cyclohept[1,2-b]-1,4-oxazin-3[2H]-one The residue from Step A was dissolved in 50 ml of dimethyl formamide and added dropwise to a solution of 0.7 g (0.0146 m) of a 50% oil dispersion of sodium hydride in 50 ml of dimethyl formamide with stirring. After stirring one hour, excess sodium hydride was decomposed by the addition of water. The mixture was extracted twice with ethyl acetate and the extract was back washed with water, dilute, cold hydrochloric acid and saturated aqueous sodium bicarbonate solution. After drying (Na$_2$SO$_4$) the ethyl acetate solution was concentrated to dryness in vacuo to provide crude product.

Step C: Preparation of trans-4-ethyl-2,3,4,4a,5,6,7,11b-octahydrobenzo[6,7]cyclohept[1,2-b]-1,4-oxazine and hydrogen maleate salt The 1,4-oxazin-3-one from Step B was dissolved in 50 ml of tetrahydrofuran and added dropwise to 0.3 g (0.008 m) of lithium aluminum hydride in 50 ml of tetrahydrofuran. The mixture was heated at reflux temperature for one hour, cooled and treated with sufficient saturated aqueous sodium sulfate solution to quench excess lithium aluminum hydride. The mixture was filtered and concentrated to dryness in vacuo. The residue was dissolved in methylene chloride, dried (Na$_2$SO$_4$), and concentrated to dryness in vacuo to a residue of crude product (2.1 g, 81%). The maleate salt was prepared by treating with a stoichiometric amount of maleic acid in a minimum of warm isopropanol and adding ether to the cooled solution to incipient cloudiness. After precipitation was complete the salt was collected and recrystallized from benzene to give trans-4-ethyl-2,3,4,4a,5,6,7,11b-octahydrobenzo[6,7]cyclohept[1,2-b]-1,4-oxazine hydrogen maleate, m.p. 132°–135° C.

Following the procedure substantially as described in Example 1, Steps A, B and C but substituting for the starting material used in Step A thereof, an equimolecular amount of the compounds of structure III described in Table I, there are obtained the corresponding compounds of structure I also described in Table I in accordance with the following reaction sequence:

TABLE I

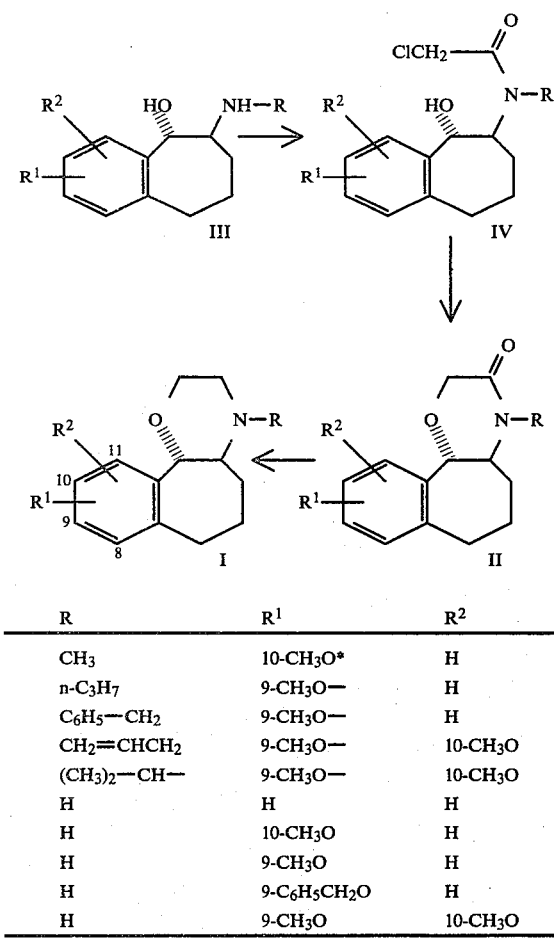

| R | R$^1$ | R$^2$ |
|---|---|---|
| CH$_3$ | 10-CH$_3$O* | H |
| n-C$_3$H$_7$ | 9-CH$_3$O— | H |
| C$_6$H$_5$—CH$_2$ | 9-CH$_3$O— | H |
| CH$_2$=CHCH$_2$ | 9-CH$_3$O— | 10-CH$_3$O |
| (CH$_3$)$_2$—CH— | 9-CH$_3$O— | 10-CH$_3$O |
| H | H | H |
| H | 10-CH$_3$O | H |
| H | 9-CH$_3$O | H |
| H | 9-C$_6$H$_5$CH$_2$O | H |
| H | 9-CH$_3$O | 10-CH$_3$O |

*numbers refer to carbon atoms in compound I

EXAMPLE 2

Trans-4-Allyl-2,3,4,4a,5,6,7,11b-octahydrobenzo[6,7-]cyclohept[1,2-b]-1,4-oxazine hydrochloride To a solution of trans 2,3,4,4a,5,6,7,11b-octahydro[6,7]cyclohept[1,2]-1,4-oxazine (1.0 g) in DMF (15 ml) was added K$_2$CO$_3$ (1.1 g) and allyl bromide (0.95 g, 0.79 mmoles). The reaction mixture was stirred at room temperature for 6 hrs, and then concentrated in vacuo to a small volume. The reaction was diluted with water (40 ml) and extracted with ether (3×100 ml). The ether layer was washed with brine, dried over Na$_2$SO$_4$ and filtered. Ethanolic hydrochloric acid was added and the salt separated to give product.

Employing the procedure substantially as described in Example 2 but substituting for the octahydrobenzo-oxazine and allyl bromide used therein, equimolecular amounts of the octahydrobenzo-oxazines and alkyl halides (R—X) described in Table II, there are produced the N-substituted compounds, also described in Table II in accordance with the following reaction:

TABLE II

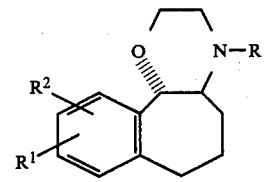

| X | R | R¹ | R² |
|---|---|---|---|
| Br | n-$C_3H_7$ | 10-$CH_3O$— | H |
| Br | $C_2H_5$ | 10-$CH_3O$— | H |
| Br | n-$C_4H_9$ | 9-$CH_3O$— | H |
| Br | n-$C_3H_7$ | 9-$CH_3O$— | H |
| Br | $C_2H_5$ | 9-$CH_3O$— | 10-$CH_3O$— |
| Br | i-$C_3H_7$ | 9-$C_6H_5CH_2O$— | H |

EXAMPLE 3

Trans-10-hydroxy-2,3,4,4a,5,6,7,11b-octahydrobenzo[6,7]cyclohept[1,2-b]-1,4-oxazine Trans-10-methoxy-2,3,4,4a,5,6,7,11b-octahydrobenzo[6,7]cyclohept[1,2-b]-1,4-oxazine (1.1 g, 0.005 m) is dissolved in 20 ml of ethanol and HBr is bubbled through the solution. The solution is concentrated in vacuo, taken up in methylene chloride and cooled in a dry ice/acetone bath. This cooled mixture is added rapidly to 2.5 g (0.001 m) of $BBr_3$ in 10 ml of methylene chloride also cooled to −78° C. The reaction mixture is allowed to slowly warm up to room temperature overnight with stirring. Methanol is added and the mixture concentrated. This methanol treatment is repeated several times in order to remove the boron contaminants. Crystallization of the residue provides trans-10-hydroxy-2,3,4,4a,5,6,7,11b-octahydro[6,7]cyclohept[1,2-b]-1,4-oxazine hydrobromide.

Employing the procedure substantially as described in Example 3, but substituting for the trans-10-methoxy-2,3,4,4a,5,6,7,11b-octahydrobenzo[6,7]cyclohept-[1,2-b]-1,4-oxazine used therein, equimolecular amounts of the alkoxy substituted compounds identified in Table III, there are produced the corresponding hydroxy substituted compounds, also identified in Table III in accordance with the following reaction:

TABLE III

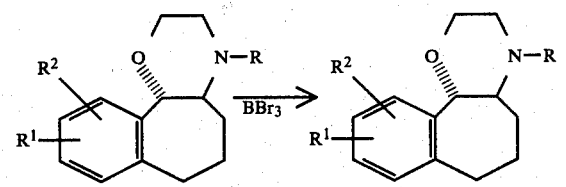

R¹ and/or R² = alkylo—            R¹ and/or R² = HO

| R¹ | R² | R | R¹ | R² |
|---|---|---|---|---|
| 10-$CH_3O$— | H | $CH_3$— | 10-HO— | H |
| 9-$CH_3O$— | H | n-$C_3H_7$— | 9-HO— | H |
| 9-$CH_3O$— | 10-$CH_3O$— | $CH_2$=CH—$CH_2$— | 9-HO— | 10-HO— |
| 9-$CH_3O$— | H | H | 9-HO— | H |
| 9-$CH_3O$— | 10-$CH_3O$— | H | 9-HO— | 10-HO— |
| 10-$CH_3O$— | H | $C_2H_5$— | 10-HO— | H |
| 9-$CH_3O$— | H | n-$C_4H_9$— | 9-HO— | H |
| 9-$CH_3O$— | H | n-$C_3H_7$— | 9-HO— | H |
| 9-$CH_3O$— | 10-$CH_3O$— | $C_2H_5$ | 9-HO— | 10-HO |
| 10-$CH_3O$— | H | n-$C_3H_7$ | 10-HO— | H |

EXAMPLE 4

Pharmaceutical Composition

A typical table containing 100 mg of active ingredient per tablet is prepared by mixing together with the active ingredient calcium phosphate, lactose and starch in the amounts shown in the table below. After these ingredients are thoroughly mixed, the appropriate amount of magnesium stearate is added and the dry mixture blended for an additional three minutes. This mixture is then compressed into tablets.

| Tablet Formula | |
|---|---|
| Ingredient | Mg. per Tablet |
| Trans-4-Ethyl-2,3,4,4a,5,6,7,11b-octahydrobenzo[6,7]cyclohept[1,2-b] [1,4]oxazine hydrogen maleate salt | 100 mg |
| Calcium phosphate | 52 mg |
| Lactose | 60 mg |
| Starch | 10 mg |
| Magnesium stearate | 1 mg |

Similarly prepared are tablets comprising as active ingredient any of the other novel compounds described herein.

What is claimed is:

1. A compound of structural formula:

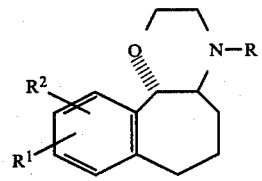

or a pharmaceutically acceptable salt thereof, wherein R is $C_{1-4}$ alkyl, $C_{2-5}$ alkenyl, or phenyl-$C_{1-4}$ alkyl; and R¹ and R² are independently hydrogen, $C_{1-4}$ alkoxy, phenyl-$C_{1-4}$ alkoxy or hydroxy.

2. The compound of claim 1, wherein R is hydrogen, ethyl or propyl, and R¹ and R² are independently hydrogen, methoxy or hydroxy.

3. A compound of claim 1, wherein R is hydrogen, ethyl or propyl, and R¹ is 10-hydroxy, and R² is hydrogen.

4. A pharmaceutical formulation for the treatment of depression or hypertension comprising a pharmaceutical carrier and an effective amount of a compound of structural formula:

or a pharmaceutically acceptable salt thereof, wherein R is $C_{1-4}$ alkyl, $C_{2-5}$ alkenyl, or phenyl-$C_{1-4}$ alkyl; and R¹ and R² are independently hydrogen, $C_{1-4}$ alkoxy, phenyl-$C_{1-4}$ alkoxy or hydroxy.

5. The formulation of claim 4, wherein R is hydrogen, ethyl or propyl, and $R^1$ and $R^2$ are independently hydrogen, methoxy or hydroxy.

6. The formulation of claim 4, wherein R is hydrogen, ethyl or propyl, and $R^1$ is 10-hydroxy, and $R^2$ is hydrogen.

7. A method of treating hypertension or depression which comprises the administration to a patient in need of treatment of an effective amount of a compound of structural formula:

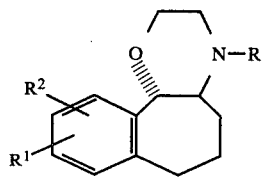

wherein R is $C_{1-4}$ alkyl, $C_{2-5}$ alkenyl, or phenyl-$C_{1-4}$ alkyl; and $R^1$ and $R^2$ are independently hydrogen, $C_{1-4}$ alkoxy, phenyl-$C_{1-4}$ alkoxy or hydroxy.

8. The method of claim 7, wherein R is hydrogen, ethyl or propyl, and $R^1$ and $R^2$ are independently hydrogen, methoxy or hydroxy.

9. A method of claim 7, wherein R is hydrogen, ethyl or propyl, and $R^1$ is 10-hydroxy, and $R^2$ is hydrogen.

* * * * *